(12) United States Patent
Teschner et al.

(10) Patent No.: US 8,709,492 B2
(45) Date of Patent: Apr. 29, 2014

(54) PROCESS FOR PRODUCING A PLASMA PROTEIN-CONTAINING MEDICAMENT WITH REDUCED CONCENTRATION OF CITRATE AND METALS

(75) Inventors: Wolfgang Teschner, Vienna (AT); Yendra Linnau, Vienna (AT); Sonja Svatos, Berg (AT); Herwig Igel, Vienna (AT)

(73) Assignee: Baxter Aktiengesellschaft (AT)

( * ) Notice: Subject to any disclaimer, the term of this patent is extended or adjusted under 35 U.S.C. 154(b) by 1177 days.

(21) Appl. No.: 11/151,295

(22) Filed: Jun. 14, 2005

(65) Prior Publication Data
US 2005/0249815 A1 Nov. 10, 2005

Related U.S. Application Data

(63) Continuation of application No. 09/254,288, filed as application No. PCT/AT97/00197 on Sep. 10, 1997, now abandoned.

(30) Foreign Application Priority Data

Sep. 16, 1996 (AT) .................................. A 1633/96

(51) Int. Cl.
*A61K 35/16* (2006.01)
(52) U.S. Cl.
USPC ......................................................... 424/530
(58) Field of Classification Search
None
See application file for complete search history.

(56) References Cited

U.S. PATENT DOCUMENTS

| | | | | |
|---|---|---|---|---|
| 5,118,794 A | 6/1992 | Grangeorge et al. | .......... | 530/363 |
| 5,229,498 A | 7/1993 | Eketorp | ........................ | 530/364 |
| 5,372,997 A | 12/1994 | Inoue et al. | ..................... | 514/21 |
| 5,561,115 A | 10/1996 | Tenold | ............................ | 514/21 |
| 5,744,586 A * | 4/1998 | Rolf et al. | ..................... | 530/394 |
| 5,846,930 A | 12/1998 | Debart et al. | ..................... | 514/2 |

FOREIGN PATENT DOCUMENTS

| | | |
|---|---|---|
| EP | 0484464 | 1/1996 |
| EP | 0696595 | 2/1996 |
| EP | 0787498 | 8/1997 |
| EP | 0893450 | 1/1999 |

OTHER PUBLICATIONS

Definition of "substantial" from the American Heritage Dictionary, Fourth Edition, 2006.*
Thermo Scientific Catalog, http://www.piercenet.com/browse.cfm?fldID=7FAD146E-B43B-4110-9F71-7F749D41BEC5, acessed Feb. 26, 2010, 2 pages.*
Cohn et al., "Preparation and Properties of Serum and Plasma Proteins. IV. A System for the Separation into FRactions of the Protein and Lipoprotein Components of Biological Tissues and Fluids", JACS 68 : 459-475 (1946).*

\* cited by examiner

*Primary Examiner* — Sandra Saucier
(74) *Attorney, Agent, or Firm* — Perkins Coie LLP

(57) ABSTRACT

There is disclosed a method of preparing a plasma-protein-containing medicament from citrated plasma or from a citrate-containing plasma fraction, the medicament being substantially free from undesired metals, which method comprises the following steps:
exchanging the citrate and optionally citrate-bound metals in a plasma-protein-containing solution for a water-soluble mono- or dicarboxylate or for an organic mono- or dicarboxylic acid under non-precipitating conditions, recovering the plasma protein or the plasma proteins, and finishing the medicament.

32 Claims, No Drawings

PROCESS FOR PRODUCING A PLASMA PROTEIN-CONTAINING MEDICAMENT WITH REDUCED CONCENTRATION OF CITRATE AND METALS

This application is a continuation of U.S. Ser. No. 09/254,288, filed Apr. 2, 1999, which was a national stage application of PCT/AT97/00197, filed Sep. 10, 1997. These applications are hereby incorporated by reference.

FIELD OF THE INVENTION

The invention relates to a method of preparing a plasma protein-containing medicament from citrated plasma or from a citrate-containing plasma fraction, the medicament being substantially free from undesired metals.

BACKGROUND OF THE INVENTION

With a concentration of 35-50 g/l, human albumin is the main component in plasma. Its therapeutic use has been known for a long time, an administration of albumin being indicated, e.g., in case of an acute loss of blood or plasma or in case of failure of the vasomotoric regulation. Since the osmotic pressure of a 20% (25%) albumin solution is approximately 4 times (5 times) that of normal human serum, the effect of albumin is mainly based on its ability to maintain the osmotic pressure.

Human albumin preparations are prepared from human plasma by multiple fractionation, e.g. by a fractionation according to Cohn, or they are prepared by means of recombinant methods. On account of various materials used during its preparation or when the albumin solution is stored in glass containers, aluminum gets into the albumin preparation so that the final content of aluminum in the respective preparations may be quite substantial.

Aluminum, which constitutes one of the most frequently occurring elements in nature, has recently been increasingly associated with various diseases of the human body, primarily with diseases of the nervous and bone systems. Although the lungs and the gastro-intestinal tract form an efficient barrier for the uptake of aluminum, this barrier is no longer effective in patients receiving intravenous preparations, and the aluminum possibly present in the administered preparations may be taken up without hindrance. Thus, e.g., D. S. Milliner et al. (N. Engl. J. Med. (1985), 312, pp. 165-167) report that some albumin products comprising large amounts of aluminum have lead to diseases of the bones or to encephalitis. Aluminum is also increasingly associated with Alzheimer's disease.

Therefore, efforts have been made to keep the aluminum content of, e.g., albumin preparations low. From U.S. Pat. No. 5,372,997, e.g., a method of reducing the aluminum content of albumin preparations by using special glass containers on the one hand, and by treatment with an anion exchanger, on the other hand, has been known. The aluminum is prevented from dissolving out of glass containers by using a special glass poor in aluminum and by dealkalizing the inner surfaces thereof with an ammonium sulfate solution or with sulphurous acid. Furthermore, a treatment with a cation exchanger is carried out. Finally, for heat-treating the albumin solution, the stabilizers commonly used therefor, such as sodium N-acetyl tryptophane or sodium caprylate, are admixed.

From EP-0 484 464-B1 a method of purifying an albumin from multivalent metal ions bound thereto by substituting them by monovalent metal ions, e.g. ammonium or alkaline metal ions, has been known.

Also from U.S. Pat. No. 5,250,663 a method has been known according to which an albumin substantially free from aluminum can be obtained. This method starts with an albumin-containing fraction, a Cohn fraction, e.g., and at first various precipitations are carried out. I. a., a heat shock treatment is carried out in the presence of sodium caprylate as stabilizer and 10 to 20% ethanol. Finally, this solution is subjected to an ultrafiltration and a diafiltration. After the diafiltration, aluminum and other impurities have been removed, weak salt solutions, such as 3% NaCl, sodium acetate or, in some instances, sodium caprylate solutions being used for this diafiltration. With this use of caprylate, no exchange of salts will occur, since caprylate has already been admixed as a stabilizer for the heat shock treatment prior to diafiltration; thus, substantial amounts of citrate ions will still be present in the preparation.

As has, e.g., been described by J. C. May et al. (1992) (Vox Sang., 62, pp. 65-69), the presence of citrate ions, which have a high affinity to aluminum, plays an essential role in the uptake of aluminum (for this, cf. e.g. also R. B. Martin (1986), J. Inorgan. Biochem., 28, pp. 181-187), and thus the mere presence of citrate ions constitutes a general risk of metal ion contaminations for all the preparations.

In EP-0 696 595-A1, the citrate ions are removed in the course of a DEAE Sephadex chromatography in a method in which caprylate is used for the fractionation of albumin. Yet there is no simple exchange of citrate ions for other ions, but—on account of the high costs of the DEAE Sephadex anion exchangers—an expensive separation of citrate takes place.

SUMMARY OF THE INVENTION

The present invention has as its object to provide a novel and simple method of avoiding or reducing, respectively, undesired metals in plasma-protein-containing medicaments, in which both, the undesired metals are removed in the course of the preparation method and a contamination of the finished preparations during storage in metal-containing containers is prevented or reduced, respectively.

According to the invention, this object is achieved by a method of the initially defined kind which comprises the following steps:
exchanging the citrate and optionally citrate-bound metals in a plasma-protein-containing solution for a water-soluble mono- or dicarboxylate or for an organic mono- or dicarboxylic acid under non-precipitating conditions, recovering the plasma protein or the plasma proteins, and finishing the medicament.

Surprisingly, it has been found that it is just the anions contained in the plasma-protein-containing solution which decisively contribute to the removal of the metal cations.

DETAILED DESCRIPTION OF THE INVENTION

Contrary to the method described in U.S. Pat. No. 5,250,663, it is not only sodium caprylate which is added to a citrate-containing solution or to a citrate-containing precipitate, but the citrate which, on the one hand may carry bound metal ions in complexed form and, on the other hand, is responsible for the dissolving out of undesired metals within the course of the preparation method or during the storage of the finished medicament, is replaced by a water-soluble mono- or dicarboxylate.

For it has been shown that if citrate ion-containing preparations are precipitated and subsequently taken up in a citrate ion free buffer, the new solution may still contain considerable portions of citrate ions. Since most of the fractionation methods in the recovery of pharmaceutical preparations from plasma—to which nearly always citrate is added during the extraction—comprise one or several precipitation steps, the inventive exchange method for citrate ions thus constitutes an interesting possibility for a simple, low-cost and efficient removal of citrate ions which can easily be incorporated into already established procedures.

As the plasma fraction, e.g. a fraction obtained according to the Cohn fractionation, will serve. For the preparation of albumin, e.g., an albumin-containing precipitate from the Cohn fractionation is used.

To allow for as complete an exchange of the citrate as possible, the exchange step thus must be carried out under non-precipitating conditions, since otherwise—as has been mentioned—there will be a risk that the citrate can be removed only insufficiently because of its high affinity to the precipitated protein. Preferably, the exchange of the citrate will take place at an early time in the preparation method.

According to a preferred embodiment of the method according to the invention, as the plasma-protein-containing medicament a medicament comprising one or several factors of coagulation and fibrinolysis, immunoglobulins, glycoproteins and/or albumin, is prepared. There, in particular fibrinogen, prothrombin, the factors V, VII, VIII, IX, X, XI, XII and XIII, optionally in their activated form, von Willebrand factor, but also anticoagulants, such as heparin, heparinoids or cumarin derivatives, or fibrinolytic agents, such as streptokinase, urokinase, pro-urokinase, t-PA or plasmin, can be considered as the coagulation and fibrinolysis factors. As the immunoglobulins, various preparations comprising immunoglobulins of the classes IgG, IgA, IgM and mixtures thereof, optionally in high titers, may be prepared.

As the glycoprotein, orosomucoid may, e.g., be used.

Preferably, a salt of an organic carboxylic acid having 2 to 20 carbon atoms is used for the exchange of the citrate, a caprylate or a tartrate or mixtures thereof being particularly preferred.

For the purposes of the present invention, also an organic mono- or dicarboxylic acid is to be understood as a mono- or dicarboxylate, since in any case the exchange of the citrate in solution will always be for the anion of the acid. Preferably, an organic mono- or dicarboxylic acid having 2 to 4 carbon atoms is used for exchanging the citrate.

The method according to the invention has proved particularly suitable for the preparation of plasma-protein-containing medicaments that exhibit excellent properties particularly in respect of their aluminum contamination by being substantially free from any detectable aluminum.

As has been mentioned, exchanging of the citrate must be effected under non-precipitating conditions. Preferably, the exchange step is effected during a diafiltration, ultrafiltration or during a chromatographic process, since these steps have proved particularly suitable for a simple, low-cost and efficient exchange.

The conditions during the exchange step depend on the method used and in particular will be chosen such that the exchange of the citrate and optionally also of citrate-bound metals will be as complete as possible. Therefore, the respective parameter which determine the method, in particular the temperature, the duration of the exchange step and the concentration of the respective mono- or dicarboxylate or mono- or dicarboxylic acid, respectively, have to be optimized.

During the exchange, the temperature will preferably be in a range of between 0 and 50° C., more preferred in a range of between 10 and 30° C., most preferred approximately at room temperature. The respective period of time for the exchange is particularly dependent on the ratio of the volume to be exchanged to the membrane surface and on the temperature and preferably is at least 30 minutes, in particular the period of time will be in a range of between 30 minutes and several hours.

In general, a parameter like the period of time will just as well depend on the respective exchange volume of the material in question. Preferably, the exchange volume will be at least 5 times, most preferred at least 30 times that of the starting solution, and the period of time for the exchange will be chosen accordingly.

The concentration of mono- or dicarboxylate or of mono- or dicarboxylic acid preferably is in a range of between 0.001 and 10 mol/l, most preferred in a range of between 0.001 and 1 mol/l.

Sodium caprylate, e.g., is added at a concentration of between 1.0 mmol/l and 1.5 mol/l, preferably in a range of between 1.0 mmol/l and 25 mmol/l.

Sodium acetate, e.g., is added at a concentration of between 1 mmol/l and 5.5 mol/l, preferably between 50 mmol/l and 1.0 mol/l.

The sodium salt of the hexanoic acid, e.g., is added at a concentration of between 1.0 mmol/l and 1.0 mol/l, preferably in a range of between 5.0 mmol/l and 0.1 mol/l.

Sodium tartrate may be added at a concentration of between 1.0 mmol/l and 1.2 mol/l, preferably between 10.0 mmol/l and 0.2 mol/l.

For salts of higher acids, thus the efficient amounts can already be found in a range of from 0.001 to 0.1 mol/l, while salts of lower acids preferably are added at somewhat higher concentrations.

A further parameter which is decisive for the method is the pH of the solution. Preferably, it is at pH 6 to 8, most preferred at pH 6.5 to 7.5.

Beside carboxylate or carboxylic acid, respectively, also inorganic salts, such as, e.g., sodium or potassium salts, may be contained in the solution for increasing the ionic strength thereof. For instance, an at least 4% sodium chloride solution is contained. Furthermore, various buffer salts may be contained.

As the materials for the respective exchange method, in particular commercially available materials, such as, e.g., diafiltration membranes, ultrafiltration units, various chromatographic gels, molecular sieves and others may be used. All these materials may be based on organic or inorganic materials; they may be of synthetic of biological origin.

It has been shown that the method according to the invention will be particularly advantageous if the plasma-protein-containing solution is purified and/or concentrated before the exchange.

As with all the medicaments based on plasma as raw material, one or several steps for inactivating possibly present viruses should also be provided within the scope of the preparation method according to the invention.

A preferred embodiment of the method according to the invention thus relates to a method in which the plasma-protein-containing solution is treated, preferably heat-treated, before and/or after the exchange so as to inactivate possibly present viruses. Common virus inactivation treatments which may be used within the scope of the present method have been described in EP-0 159 311, EP-0 519 901 or in EP-0 674 531.

It is particularly suitable if prior to a virus inactivation treatment, the plasma protein recovered is further subjected to a dialyses against a medium with a low salt content, e.g. water. This may provide an additional stabilizing effect for the plasma protein because of the presence of the mono- or dicarboxylate. The recovery of the plasma protein or plasma proteins and the finishing of the medicament preferably should be effected exclusively with citrate-free components so as to avoid the renewed contamination of the preparation with citrate ions which are responsible for a renewed contamination with metal ions in case of longer storage.

It is true that the method according to the invention has proved quite particularly suitable for removing aluminum ions or for preventing a renewed contamination with aluminum ions, respectively, during storage of the medicament. Yet also other metal ions from which it is known that they may contaminate plasma-protein-containing medicaments, such as aluminum-like metals, cadmium, zinc, lead, iron and others, may efficiently be reduced.

Thus, an object of the present invention is also a plasma-protein-containing medicament which is obtainable according to the method of the invention and has a content of undesired metal of less than 100 µg/l, preferably less than 10 µg/l, in particular less than 200 µg/l, determined, e.g., by atomic absorption spectroscopy, this maximum content not being exceeded even after extended storage, even when stored for more than 5 years.

The plasma-protein-containing medicament of the invention may be stored in the most varying containers of the prior art. Such containers may consist of glass, synthetic material, metals or combinations thereof. The containers may also be specially pre-treated; thus, the surface may have been siliconized, e.g. As the glasses, both hard glasses and soft glasses (cf. e.g. glasses of the classification USP 23, p. 1781) may be used.

In particular, the plasma-protein-containing medicament of the invention has a low content of undesired metals when stored in hard glasses; particularly preferred the latter is less than 100 µg/l, more preferred less than 10 µg/l, most preferred less than 200 µg/l.

The present invention will be explained in more detail by way of the following examples to which, however, it shall not be restricted.

Example 1

A precipitate of Cohn fractionation comprising albumin in a purity of >95% is dissolved 1+2 (w/v; 1 kg in 2 l) in 50 g/l NaCl solution at a neutral pH. The solution is continuously diafiltered with a regenerated cellulose membrane at +4° C. against water. At this, 0.1 mmol caprylate is added per g of protein.

In the following Table 1 a), the aluminum decrease and the citrate decrease after diafiltration without addition of a carboxylate, such as, e.g., caprylate, tartrate, salt of hexanoic acid or an acetate, are illustrated.

TABLE 1

| | a) without addition of a carboxylate: | | | |
|---|---|---|---|---|
| | Aluminum content | | Citrate content | |
| Sample | µg/g Protein | in % | µmol/g Protein | in % |
| Before diafiltration | 2.802 | 100.0 | 166 | 100.0 |
| Diaconcentrate | 0.704 | 25.1 | 8.6 | 5.2 |

The following Table 1 b) shows the aluminum decrease and the citrate decrease after diafiltration with the addition of 0.1 mmol caprylate.

| | 1 b) with the addition of caprylate | | | |
|---|---|---|---|---|
| | Aluminum content | | Citrate content | |
| Sample | µg/g Protein | in % | µmol/g Protein | in % |
| Before diafiltration | 2.999 | 100.0 | 139.5 | 100.0 |
| Diaconcentrate | 0.096 | 3.2 | 1.1 | 0.8 |

A comparison of this table with Table 1 a), i.e. with the corresponding decreases without the addition of a caprylate, clearly shows that by an 0.1 mmol caprylate addition per g of protein a clearly higher decrease of citrate and aluminum can be attained than is the case without the addition of a carboxylate, such as, e.g., caprylate.

Example 2

An albumin-containing precipitate is dissolved as described in Example 1 and subsequently diafiltered. There, 0.5 mmol of a sodium salt of the hexanoic acid were added per g of protein. After termination of the diafiltration, there result the following aluminum and citrate decreases (Table 2).

TABLE 2

| | Aluminum content | | Citrate content | |
|---|---|---|---|---|
| Sample | µg/g Protein | in % | µmol/g Protein | in % |
| Before diafiltration | 3.368 | 100.0 | 135 | 100.0 |
| Diaconcentrate | 0.127 | 3.8 | 1.8 | 1.3 |

As appears clearly from this Table as compared to Table 1 a), by an addition of 0.5 mmol of a sodium salt of hexanoic acid per g of protein, a clearly higher decrease of citrate and aluminum can be attained than is the case without the addition of the hexanoic acid salt.

Example 3

A precipitate of Cohn fractionation comprising albumin in a purity of >95% is dissolved 1+2 (w/v; 1 kg in 2 l) in 50 g/l NaCl solution at a neutral pH. The solution is continuously diafiltered with a regenerated cellulose membrane at +4° C. against water. At this, 5 mmol acetate is added per g of protein.

In the following Table 3, the aluminum decrease and the citrate decrease after diafiltration without addition of 5 mmol acetate per g of protein are illustrated.

TABLE 3

| | Aluminum content | | Citrate content | |
|---|---|---|---|---|
| Sample | µg/g Protein | in % | µmol/g Protein | in % |
| Before diafiltration | 3.95 | 100.0 | 155 | 100.0 |
| Diaconcentrate | 0.3 | 7.6 | 2.6 | 1.7 |

As appears clearly from this Table as compared to Table 1 a), by an addition of 5 mmol acetate per g of protein, a clearly higher decrease of citrate and aluminum can be attained than is the case without the addition of the acetate.

Example 4

An albumin-containing precipitate is dissolved as described in Example 1 and subsequently diafiltered. There, 1.0 mmol tartrate per g of protein is added. After termination of the diafiltration, there result the following aluminum and citrate decreases (Table 4).

TABLE 4

| Sample | Aluminum content | | Citrate content | |
|---|---|---|---|---|
| | µg/g Protein | in % | µmol/g Protein | in % |
| Before diafiltration | 6.29 | 100.0 | 129 | 100.0 |
| Diaconcentrate | 0.62 | 9.9 | 1.0 | 0.8 |

As appears clearly from this Table as compared to Table 1 a), by an addition of 1.0 mmol tartrate per g of protein, a clearly higher decrease of citrate and aluminum can be attained than is the case without the addition of the tartrate.

The invention claimed is:

1. A method of preparing a plasma-protein-containing medicament from citrated plasma or from a citrate-containing plasma fraction, wherein the medicament has a reduced concentration of undesired metals selected from the group consisting of aluminum, cadmium, zinc, lead and iron, wherein the method comprises the steps of:
    (a) obtaining citrated plasma or citrate-containing plasma fraction by Cohn fractionation;
    (b) adding to the citrated plasma or citrate-containing plasma fraction, a compound to achieve a solution having the compound concentration of between 0.001 and 1.00 mol/liter, wherein the compound is selected from the group consisting of a monocarboxylate, a dicarboxylate, a monocarboxylic acid and a dicarboxylic acid;
    (c) exchanging the citrate and citrate-bound metals that may be present in the plasma or plasma fraction with the compound by diafiltration, ultrafiltration or chromatography at a temperature above 0° C. to 50° C. and at a pH of 6 to 8, under non-precipitating conditions, thereby reducing the concentration of citrate and the undesired metals that may have been present;
    (d) recovering one or more plasma proteins; and
    (e) finishing the medicament.

2. The method as set forth in claim 1, wherein the compound has 2 to 20 carbon atoms.

3. The method as set forth in claim 1, wherein the compound is selected from the group consisting of caprylate, tartrate, hexanoic acid and acetate.

4. The method as set forth in claim 1, further comprising subjecting the citrated plasma or a citrate-containing plasma fraction to a purification procedure before the reducing.

5. The method as set forth in claim 1, further comprising subjecting the citrated plasma or a citrate-containing plasma fraction to a concentration procedure before the reducing.

6. The method as set forth in claim 1, further comprising subjecting the citrated plasma or a citrate-containing plasma fraction to a treatment for virus inactivation.

7. The method as set forth in claim 6, wherein the treatment for virus inactivation is performed before the exchanging.

8. The method as set forth in claim 6, wherein the treatment for virus inactivation is performed after the exchanging.

9. The method as set forth in claim 6, wherein the treatment for virus inactivation is performed both before and after the exchanging.

10. The method as set forth in claim 6, wherein the treatment for virus-inactivation is a heat-treatment.

11. The method as set forth in claim 6, wherein the treatment for virus inactivation is performed immediately after the recovering of at least one plasma protein.

12. The method as set forth in claim 1, wherein the finishing of the medicament is performed using only citrate-free components.

13. The method according to claim 1, wherein the exchanging occurs at a pH of 6.5 to 7.5.

14. The method according to claim 1, wherein the exchanging occurs at a temperature of 10° C. to 30° C.

15. The method according to claim 1, wherein the exchanging occurs at room temperature.

16. The method according to claim 1, wherein the plasma proteins for the medicament are selected from the group consisting of albumin, coagulation factors, fibrinolysis factors, immunoglobulins and glycoproteins.

17. A method of preparing a plasma-protein-containing medicament from a Cohn fraction comprising plasma proteins and citrate, wherein the medicament has a reduced concentration of undesired metals selected from the group consisting of aluminum, cadmium, zinc, lead and iron, wherein the method comprises the steps of:
    (a) adding to the Cohn fraction a compound to achieve a solution having the compound concentration of between 0.001 and 1.00 mol/liter, wherein the compound is selected from the group consisting of a monocarboxylate, a dicarboxylate, a monocarboxylic acid and a dicarboxylic acid;
    (b) exchanging the citrate and citrate-bound metals that may be present in the Cohn fraction with the compound by diafiltration, ultrafiltration or chromatography at a temperature above 0° C. to 50° C. and at a pH of 6 to 8, under non-precipitating conditions, thereby reducing the concentration of citrate and the undesired metals that may have been present;
    (c) recovering one or more plasma proteins; and
    (d) finishing the medicament.

18. The method as set forth in claim 17, wherein the compound has 2 to 20 carbon atoms.

19. The method as set forth in claim 17, wherein the compound is selected from the group consisting of caprylate, tartrate, hexanoic acid and acetate.

20. The method as set forth in claim 17, further comprising subjecting the plasma-protein-containing solution to a purification procedure before the exchanging.

21. The method as set forth in claim 17, further comprising subjecting the plasma-protein-containing solution to a concentration procedure before the exchanging.

22. The method as set forth in claim 17, further comprising subjecting the medicament to a treatment for virus inactivation.

23. The method as set forth in claim 22, wherein the treatment for virus inactivation is performed before the exchanging.

24. The method as set forth in claim 22, wherein the treatment for virus inactivation is performed after the exchanging.

25. The method as set forth in claim 22, wherein the treatment for virus inactivation is performed both before and after the exchanging.

26. The method as set forth in claim 22, wherein the treatment for virus-inactivation is a heat-treatment.

27. The method as set forth in claim 22, wherein the treatment for virus inactivation is performed immediately after the recovering of at least one plasma protein.

28. The method as set forth in claim 17, wherein the finishing of the medicament is performed using only citrate-free components.

29. The method according to claim 17, wherein the exchanging occurs at a pH of 6.5 to 7.5.

30. The method according to claim 17, wherein the exchanging occurs at a temperature of 10° C. to 30° C.

31. The method according to claim 17, wherein the exchanging occurs at room temperature.

32. The method according to claim 17, wherein the plasma proteins for the medicament are selected from the group consisting of albumin, coagulation factors, fibrinolysis factors, immunoglobulins and glycoproteins.

\* \* \* \* \*